United States Patent [19]
Gliner et al.

[11] Patent Number: 5,601,612
[45] Date of Patent: Feb. 11, 1997

[54] METHOD FOR APPLYING A MULTIPHASIC WAVEFORM

[75] Inventors: Bradford E. Gliner, Bellevue; Thomas D. Lyster, Bothell; Clinton S. Cole, Kirkland; Daniel J. Powers; Carlton B. Morgan, both of Bainbridge Island, all of Wash.

[73] Assignee: Heartstream, Inc., Seattle, Wash.

[21] Appl. No.: 601,234

[22] Filed: Feb. 14, 1996

Related U.S. Application Data

[62] Division of Ser. No. 103,837, Aug. 6, 1993.

[51] Int. Cl.$^6$ .................................. A61N 1/39
[52] U.S. Cl. .................. 607/7; 607/5; 607/6; 607/74
[58] Field of Search .................. 607/5, 6, 7, 2, 607/4, 62, 74

[56] References Cited

U.S. PATENT DOCUMENTS

| | | |
|---|---|---|
| 3,211,154 | 10/1965 | Becker et al. . |
| 3,241,555 | 3/1966 | Caywood et al. . |
| 3,706,313 | 12/1972 | Milani et al. . |
| 3,782,389 | 1/1974 | Bell . |
| 3,860,009 | 1/1975 | Bell et al. . |
| 3,862,636 | 1/1975 | Bell et al. . |
| 3,886,950 | 6/1975 | Ukkestad et al. . |
| 4,023,573 | 5/1977 | Pantridge et al. . |

(List continued on next page.)

FOREIGN PATENT DOCUMENTS

| | | |
|---|---|---|
| 0281219 | 9/1988 | European Pat. Off. . |
| 0315368 | 5/1989 | European Pat. Off. . |
| 0353341 | 2/1990 | European Pat. Off. . |
| 0437104 | 7/1991 | European Pat. Off. . |
| 0507504 | 10/1992 | European Pat. Off. . |
| 2070435 | 9/1981 | United Kingdom . |
| 2083363 | 3/1982 | United Kingdom . |
| 93/16759 | 9/1993 | WIPO . |
| 94/21327 | 9/1994 | WIPO . |
| 94/22530 | 10/1994 | WIPO . |

OTHER PUBLICATIONS

Alferness et al., "The influence of shock waveforms on defibrillation efficacy," *IEEE Engineering in Medicine and Biology*, pp. 25–27 (Jun. 1990).

Anderson, et al., "The Efficacy of Trapezoidal Wave Forms for Ventricular Defibrillation," *Chest* 70(2): 298–300.

Blilie et al., "Predicting and validating cardiothoracic current flow using finite element modeling," *PACE*, 15:563, abstract 219 (Apr. 1992).

(List continued on next page.)

*Primary Examiner*—William E. Kamm
*Assistant Examiner*—Kennedy J. Schaetzle
*Attorney, Agent, or Firm*— Morrison & Foerster

[57] ABSTRACT

This invention provides an external defibrillator and defibrillation method that automatically compensates for patient-to-patient impedance differences in the delivery of electrotherapeutic pulses for defibrillation and cardioversion. In a preferred embodiment, the defibrillator has an energy source that may be discharged through electrodes on the patient to provide a biphasic voltage or current pulse. In one aspect of the invention, the first and second phase duration and initial first phase amplitude are predetermined values. In a second aspect of the invention, the duration of the first phase of the pulse may be extended if the amplitude of the first phase of the pulse fails to fall to a threshold value by the end of the predetermined first phase duration, as might occur with a high impedance patient. In a third aspect of the invention, the first phase ends when the first phase amplitude drops below a threshold value or when the first phase duration reaches a threshold time value, whichever comes first, as might occur with a low to average impedance patient. This method and apparatus of altering the delivered biphasic pulse thereby compensates for patient impedance differences by changing the nature of the delivered electrotherapeutic pulse, resulting in a smaller, more efficient and less expensive defibrillator.

5 Claims, 7 Drawing Sheets

U.S. PATENT DOCUMENTS

| | | |
|---|---|---|
| 4,328,808 | 5/1982 | Charbonnier et al. . |
| 4,419,998 | 12/1983 | Heath . |
| 4,473,078 | 9/1984 | Angel . |
| 4,494,552 | 1/1985 | Heath . |
| 4,504,773 | 3/1985 | Suzuki et al. . |
| 4,574,810 | 3/1986 | Lerman . |
| 4,595,009 | 6/1986 | Leinders . |
| 4,610,254 | 9/1986 | Morgan et al. . |
| 4,619,265 | 10/1986 | Morgan et al. . |
| 4,637,397 | 1/1987 | Jones et al. . |
| 4,745,923 | 5/1988 | Winstrom . |
| 4,800,883 | 1/1989 | Winstrom . |
| 4,821,723 | 4/1989 | Baker et al. . |
| 4,840,177 | 6/1989 | Charbonnier et al. . |
| 4,848,345 | 7/1989 | Zenkich . |
| 4,850,357 | 7/1989 | Bach, Jr. .................................. 607/74 |
| 4,953,551 | 9/1990 | Mehra et al. . |
| 4,998,531 | 3/1991 | Bocchi et al. . |
| 5,078,134 | 1/1992 | Heilman et al. . |
| 5,083,562 | 1/1992 | de Coriolis et al. . |
| 5,097,833 | 3/1992 | Campos . |
| 5,107,834 | 4/1992 | Ideker et al. . |
| 5,111,813 | 5/1992 | Charbonnier et al. . |
| 5,111,816 | 5/1992 | Pless et al. . |
| 5,207,219 | 5/1993 | Adams et al. . |
| 5,215,081 | 6/1993 | Ostroff . |
| 5,222,480 | 6/1993 | Couche et al. . |
| 5,222,492 | 6/1993 | Morgan et al. . |
| 5,230,336 | 7/1993 | Fain et al. . |
| 5,237,989 | 8/1993 | Morgan et al. . |
| 5,249,573 | 10/1993 | Fincke et al. . |
| 5,275,157 | 1/1994 | Morgan et al. . |
| 5,306,291 | 4/1994 | Kroll et al. . |
| 5,334,219 | 8/1994 | Kroll . |
| 5,334,430 | 9/1994 | Berg et al. . |
| 5,352,239 | 10/1994 | Pless ........................................ 607/5 |
| 5,370,664 | 12/1994 | Morgan et al. . |
| 5,372,606 | 12/1994 | Lang et al. ................................ 607/6 |
| 5,411,526 | 5/1995 | Kroll et al. . |

OTHER PUBLICATIONS

Chapman et al., "Non–thoracotomy internal defibrillation: Improved efficacy with biphasic shocks," *Circulation*, 76:312, abstract no. 1239 (1987).

Cooper et al., "Temporal separation of the two pulses of single capacitor biphasic and dual monophasic waveforms," *Circulation*, 84(4):612, abstract no. 2433 (1991).

Cooper et al., "The effect of phase separation on biphasic waveform defibrillation," *PACE*, 16:471–482 (Mar. 1993).

Cooper et al., "The effect of temporal separation of phases on biphasic waveform defibrillation efficacy," *The Annual International Conference of the IEEE Engineering in Medicine and Biology Society*, 13(2):0766–0767 (1991).

Crampton et al., "Low–energy ventricular defibrillation and miniature defibrillators," *JAMA*, 235(21):2284 (1976).

Dahlbäck et al., "Ventricular defibrillation with square–waves," *The Lancet* (Jul. 2, 1966).

Echt et al., "Biphasic waveform is more efficacious than monophasic waveform for transthoracic cardioversion," *PACE*, 16:914, abstract no. 256 (Apr. 1993).

Feeser et al., "Strength–duration and probability of success curves for defibrillation with biphasic waveforms," *Circulation*, 82(6):2128–2141 (1990).

Guse et al., "Defibrillation with low voltage using a left ventricular catheter and four cutaneous patch electrodes in dogs," *PACE*, 14:443–451 (Mar. 1991).

Jones et al., "Defibrillator waveshape optimization," Devices and Tech. Meeting, NIH (1982).

Jones et al., "Reduced excitation threshold in potassium depolarized myocardial cells with symmetrical biphasic waveforms," *J. Mol. Cell. Cardiol.*, 17(39):XXVII, abstract no. 39 (1985).

Jones, et al., "Decreased defibrillator–induced dysfunction with biphasic rectangular waveforms," *Am. J. Physiol.*, 247:H792–796 (1984).

Jones, et al., "Improved defibrillator waveform safety factor with biphasic waveforms," *Am. J. Physiol.*, 245:H60–65 (1983).

Jude et al., "Fundamentals of Cardiopulmonary Resuscitation," F. A. Davis Company, Philadelphia PA, pp. 98–104 (1965).

Kerber, et al., "Energy, current, and success in defibrillation and cardioversion: clinical studies using an automated impedance–based method of energy adjustment," *Circulation*, 77(5) : 1038–1046 (1988).

Knickerbocker et al., "A portable defibrillator," *IEEE Trans. on Power and Apparatus Systems*, 69:1089–1093 (1963).

Kouwenhoven, "The development of the defibrillator," *Annals of Internal Medicine*, 71(3):449–458 (1969).

Langer et al., "Considerations in the development of the automatic implantable defibrillator," *Medical Instrumentation*, 10(3):163–167 (1976).

Lerman, et al., "Currency–Based Versus Energy–Based Ventricular Defibrillation: A Prospective Study," *JACC* 12(5) : 1259–1264 (1988).

Lindsay et al., "Prospective evaluation of a sequential pacing and high–energy bi–directional shock algorithm for transvenous cardioversion in patients with ventricular tachycardia," *Circulation*, 76(3):601–609 (1987).

Mirowski et al., "Clinical treatment of life threatening ventricular tachyarrhythmias with the automatic implantable defibrillator," *American Heart Journal*, 102(2):265–270 (1981).

Mirowski et al., "Termination of malignant ventricular arrhythmias with an implanted automatic defibrillator in human beings," *The New England Journal of Medicine*, 303(6):322–324 (1980).

Podolsky, "Keeping the beat alive," *U.S. News & World Report* (Jul. 22, 1991).

Product Brochure for First Medic Semi–Automatic Defibrillators (1994), Spacelabs Medical Products, 15220 N.E. 40th Street, P.O. Box 97013, Redmond, WA 98073–9713.

Product Brochure for the Shock Advisory System (1987), Physio–Control, 11811 Willows Road Northeast, P.O. Box 97006, Redmond, WA 98073–9706.

Redd (editor), "Defibrillation with biphasic waveform may increase safety, improve survival," *Medlines*, pp. 1–2 (Jun.–Jul. 1984).

Saksena et al., "A prospective evaluation of single and dual current pathways for transvenous cardioversion in rapid ventricular tachycardia," *PACE*, 10:1130–1141 (Sep.–Oct. 1987).

Saksena et al., "Developments for future implantable cardioverters and defibrillators," *PACE*, 10:1342–1358 (Nov.–Dec. 1987).

Schuder "The role of an engineering oriented medical research group in developing improved methods and devices for achieving ventricular defibrillation: The University of Missouri experience," *PACE*, 16:95–124 (Jan. 1993).

Schuder et al. "Comparison of effectiveness of relay–switched, one–cycle quasisinusoidal waveform with critically damped sinusoid waveform in transthoracic defibrillation of 100–kilogram calves," *Medical Instrumentation*, 22(6):281–285 (1988).

Schuder et al., "A multielectrode–time sequential laboratory defibrillator for the study of implanted electrode systems," *Amer. Soc. Artif. Int. Organs*, XVIII:514–519 (1972).

Schuder et al., "Development of automatic implanted defibrillator," Devices & Tech. Meeting NIH (1981).

Schuder, et al., "One–Cycle Bidirectional Rectangular Wave Shocks for Open Chest Defibrillation in the Calf," *Abs. Am. Soc. Aftif. Intern. Organs*, 9: 16.

Schuder, et al., "Transthoracic Ventricular Defibrillation with Square–wave Stimuli: One half Cycle," *Circ. Res., XV*: 258–264 (1964).

Schuder, et al., "Defibrillation of 100 kg calves with assymetrical, bidirectional, retangular pulses," *Card. Res.*, 18:419–426 (1984).

Schuder, et al., "Transthoracic Ventricular Defibrillation in the 100 kg Calf with Symetrical One–Cycle Bidirectional Rectangular Wave Stimuli," *IEEE Trans. BME*, 30(7): 415–422 (1983).

Schuder, et al., "Ultrahigh–energy hydrogen thyraton/SCR Biderectional waveform defibrillator," *Med. & Biol. Eng. & Comput.*, 20: 419–424 (1982).

Schuder, et al., "Wave form Dependency in Defibrillating 100 kg Calves," Devices & Tech. Meeting, NIH (1981).

Schuder et al., "Waveform dependency in defibrillation," Devices & Tech. Meeting NIH (1981).

Stanton et al., "Relationship between defibrillation threshold and upper limit of vulnerability in humans," *PACE*, 15:563, abstract 221 (Apr. 1992).

Tang et al., "Ventricular defibrillation using biphasic waveforms: The importance of phasic duration," *JACC*, 13(1):207–214 (1989).

Tang, et al., "Strength Duration Curve for Ventricular Defibrillation Using Biphasic Waveforms," *PACE*, abstract no. 49 (1987).

Tang, et al., "Ventricular Defibrillation Using Biphasic Waveforms of Different Phasic Duration," *PACE*, abstract no. 47 (1987).

Walcott et al., "Comparison of monophasic, biphasic, and the edmark waveform for external defibrillation," *PACE*, 15:563, abstract 218 (Apr. 1992).

Wathen et al., "Improved defibrillation efficacy using four nonthoracotomy leads for sequential pulse defibrillation," *PACE*, 15:563, abstract 220 (Apr. 1992).

Wetherbee, et al., "Subcutaneous Patch Electrode – A Means to Obviate Thoracotomy for Implantation of the Automatic Implantable cardioverter Defibrillation System?," *Circ.*, 72: III–384, abstract no. 1536 (1985).

Winkle "The implantable defibrillator in ventricular arrhythmias," *Hospital Practice*, pp. 149–165 (Mar. 1983).

Winkle et al., "Improved Low Energy Defibrillation Efficacy in Man Using a Biphasic Truncated Exponential Waveform," *JACC*, 9(2): 142A (1987).

Zipes, "Sudden cardiac death," *Circulation*, 85(1):160–166 (1992).

METHOD FOR APPLYING A MULTIPHASIC WAVEFORM

This application is a divisional of application Ser. No. 08/103,837 filed Aug. 06, 1993.

BACKGROUND OF THE INVENTION

This invention relates generally to an electrotherapy method and apparatus for delivering a shock to a patient's heart. In particular, this invention relates to a method and apparatus for using an external defibrillator to deliver a biphasic defibrillation shock to a patient's heart through electrodes attached to the patient.

Defibrillators apply pulses of electricity to a patient's heart to convert ventricular arrhythmias, such as ventricular fibrillation and ventricular tachycardia, to normal heart rhythms through the processes of defibrillation and cardioversion, respectively. There are two main classifications of defibrillators: external and implanted. Implantable defibrillators are surgically implanted in patients who have a high likelihood of needing electrotherapy in the future. Implanted defibrillators typically monitor the patient's heart activity and automatically supply electrotherapeutic pulses directly to the patient's heart when indicated. Thus, implanted defibrillators permit the patient to function in a somewhat normal fashion away from the watchful eye of medical personnel.

External defibrillators send electrical pulses to the patient's heart through electrodes applied to the patient's torso. External defibrillators are useful in the emergency room, the operating room, emergency medical vehicles or other situations where there may be an unanticipated need to provide electrotherapy to a patient on short notice. The advantage of external defibrillators is that they may be used on a patient as needed, then subsequently moved to be used with another patient. However, because external defibrillators deliver their electrotherapeutic pulses to the patient's heart indirectly (i.e., from the surface of the patient's skin rather than directly to the heart), they must operate at higher energies, voltages and/or currents than implanted defibrillators. The high energy, voltage and current requirements have made current external defibrillators large, heavy and expensive, particularly due to the large size of the capacitors or other energy storage media required by these prior art devices.

The time plot of the current or voltage pulse delivered by a defibrillator shows the defibrillator's characteristic waveform. Waveforms are characterized according to the shape, polarity, duration and number of pulse phases. Most current external defibrillators deliver monophasic current or voltage electrotherapeutic pulses, although some deliver biphasic sinusoidal pulses. Some prior art implantable defibrillators, on the other hand, use truncated exponential, biphasic waveforms. Examples of biphasic implantable defibrillators may be found in U.S. Pat. No. 4,821,723 to Baker, Jr., et al.; U.S. Pat. No. 5,083,562 to de Coriolis et al.; U.S. Pat. No. 4,800,883 to Winstrom; U.S. Pat. No. 4,850,357 to Bach, Jr.; and U.S. Pat. No. 4,953,551 to Mehra et al.

Because each implanted defibrillator is dedicated to a single patient, its operating parameters, such as electrical pulse amplitudes and total energy delivered, may be effectively titrated to the physiology of the patient to optimize the defibrillator's effectiveness. Thus, for example, the initial voltage, first phase duration and total pulse duration may be set when the device is implanted to deliver the desired amount of energy or to achieve that desired start and end voltage differential (i.e, a constant tilt).

In contrast, because external defibrillator electrodes are not in direct contact with the patient's heart, and because external defibrillators must be able to be used on a variety of patients having a variety of physiological differences, external defibrillators must operate according to pulse amplitude and duration parameters that will be effective in most patients, no matter what the patient's physiology. For example, the impedance presented by the tissue between external defibrillator electrodes and the patient's heart varies from patient to patient, thereby varying the intensity and waveform shape of the shock actually delivered to the patient's heart for a given initial pulse amplitude and duration. Pulse amplitudes and durations effective to treat low impedance patients do not necessarily deliver effective and energy efficient treatments to high impedance patients.

Prior art external defibrillators have not fully addressed the patient variability problem. One prior art approach to this problem was to provide the external defibrillator with multiple energy settings that could be selected by the user. A common protocol for using such a defibrillator was to attempt defibrillation at an initial energy setting suitable for defibrillating a patient of average impedance, then raise the energy setting for subsequent defibrillation attempts in the event that the initial setting failed. The repeated defibrillation attempts require additional energy and add to patient risk. What is needed, therefore, is an external defibrillation method and apparatus that maximizes energy efficiency (to minimize the size of the required energy storage medium) and maximizes therapeutic efficacy across an entire population of patients.

SUMMARY OF THE INVENTION

This invention provides an external defibrillator and defibrillation method that automatically compensates for patient-to-patient impedance differences in the delivery of electrotherapeutic pulses for defibrillation and cardioversion. In a preferred embodiment, the defibrillator has an energy source that may be discharged through electrodes on the patient to provide a biphasic voltage or current pulse. In one aspect of the invention, the first and second phase duration and initial first phase amplitude are predetermined values. In a second aspect of the invention, the duration of the first phase of the pulse may be extended if the amplitude of the first phase of the pulse fails to fall to a threshold value by the end of the predetermined first phase duration, as might occur with a high impedance patient. In a third aspect of the invention, the first phase ends when the first phase amplitude drops below a threshold value or when the first phase duration reaches a threshold time value, whichever comes first, as might occur with a low to average impedance patient. This method and apparatus of altering the delivered biphasic pulse thereby compensates for patient impedance differences by changing the nature of the delivered electrotherapeutic pulse, resulting in a smaller, more efficient and less expensive defibrillator.

DETAILED DESCRIPTION OF THE PREFERRED EMBODIMENT

Figure 1:
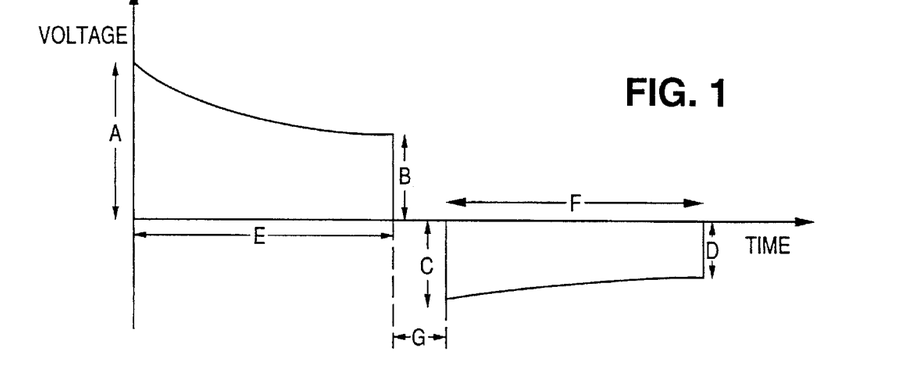
FIG. 1 is a schematic representation of a low-tilt biphasic electrotherapeutic waveform according to a first aspect of this invention.
Figure 2:
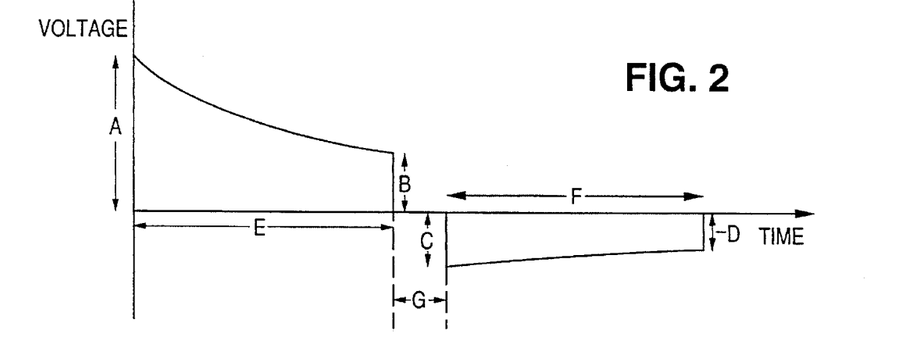
FIG. 2 is a schematic representation of a high-tilt biphasic electrotherapeutic waveform according to the first aspect of this invention.

FIGS. 1 and 2 illustrate the patient-to-patient differences that an external defibrillator design must take into account. These figures are schematic representations of truncated exponential biphasic waveforms delivered to two different patients from an external defibrillator according to the electrotherapy method of this invention for defibrillation or cardioversion. In these drawings, the vertical axis is voltage, and the horizontal axis is time. The principles discussed here are applicable to waveforms described in terms of current versus time as well, however.

The waveform shown in FIG. 1 is called a low-tilt waveform, and the waveform shown in FIG. 2 is called a high-tilt waveform, where tilt H is defined as a percent as follows:

$$H = |A| - |D|/|A| \times 100$$

As shown in FIGS. 1 and 2, A is the initial first phase voltage and D is the second phase terminal voltage. The first phase terminal voltage B results from the exponential decay over time of the initial voltage A through the patient, and the second phase terminal voltage D results from the exponential decay of the second phase initial voltage C in the same manner. The starting voltages and first and second phase durations of the FIG. 1 and FIG. 2 waveforms are the same; the differences in end voltages B and D reflect differences in patient impedance.

Prior art disclosures of the use of truncated exponential biphasic waveforms in implantable defibrillators have provided little guidance for the design of an external defibrillator that will achieve acceptable defibrillation or cardioversion rates across a wide population of patients. The defibrillator operating voltages and energy delivery requirements affect the size, cost, weight and availability of components. In particular, operating voltage requirements affect the choice of switch and capacitor technologies. Total energy delivery requirements affect defibrillator battery and capacitor choices.

We have determined that, for a given patient, externally-applied truncated exponential biphasic waveforms defibrillate at lower voltages and at lower total delivered energies than externally-applied monophasic waveforms. In addition, we have determined that there is a complex relationship between total pulse duration, first to second phase duration ratio, initial voltage, total energy and total tilt.

Up to a point, the more energy delivered to a patient in an electrotherapeutic pulse, the more likely the defibrillation attempt will succeed. Low-tilt biphasic waveforms achieve effective defibrillation rates with less delivered energy than high-tilt waveforms. However, low-tilt waveforms are energy inefficient, since much of the stored energy is not delivered to the patient. On the other hand, defibrillators delivering high-tilt biphasic waveforms deliver more of the stored energy to the patient than defibrillators delivering low-tilt waveforms while maintaining high efficacy up to a certain critical tilt value. Thus, for a given capacitor, a given initial voltage and fixed phase durations, high impedance patients receive a waveform with less total energy and lower peak currents but better conversion properties per unit of energy delivered, and low impedance patients receive a waveform with more delivered energy and higher peak currents. There appears to be an optimum tilt range in which high and low impedance patients will receive effective and efficient therapy. An optimum capacitor charged to a predetermined voltage can be chosen to deliver an effective and efficient waveform across a population of patients having a variety of physiological differences.

This invention is a defibrillator and defibrillation method that takes advantage of this relationship between waveform tilt and total energy delivered in high and low impedance patients. In one aspect of the invention, the defibrillator operates in an open loop, i.e., without any feedback regarding patient impedance parameters and with preset pulse phase durations. The preset parameters of the waveforms shown in FIG. 1 and 2 are therefore the initial voltage A of the first phase of the pulse, the duration E of the first phase, the interphase duration G, and the duration F of the second phase. The terminal voltage B of the first phase, the initial voltage C of the second phase, and the terminal voltage D of the second phase are dependent upon the physiological parameters of the patient and the physical connection between the electrodes and the patient.

For example, if the patient impedance (i.e., the total impedance between the two electrodes) is high, the amount of voltage drop (exponential decay) from the initial voltage A to the terminal voltage B during time E will be lower (FIG. 1) than if the patient impedance is low (FIG. 2). The same is true for the initial and terminal voltages of the second phase during time F. The values of A, E, G and F are set to optimize defibrillation and/or cardioversion efficacy across a population of patients. Thus, high impedance patients receive a low-tilt waveform that is more effective per unit of delivered energy, and low impedance patients receive a high-tilt waveform that delivers more of the stored energy and is therefore more energy efficient.

Figure 3:
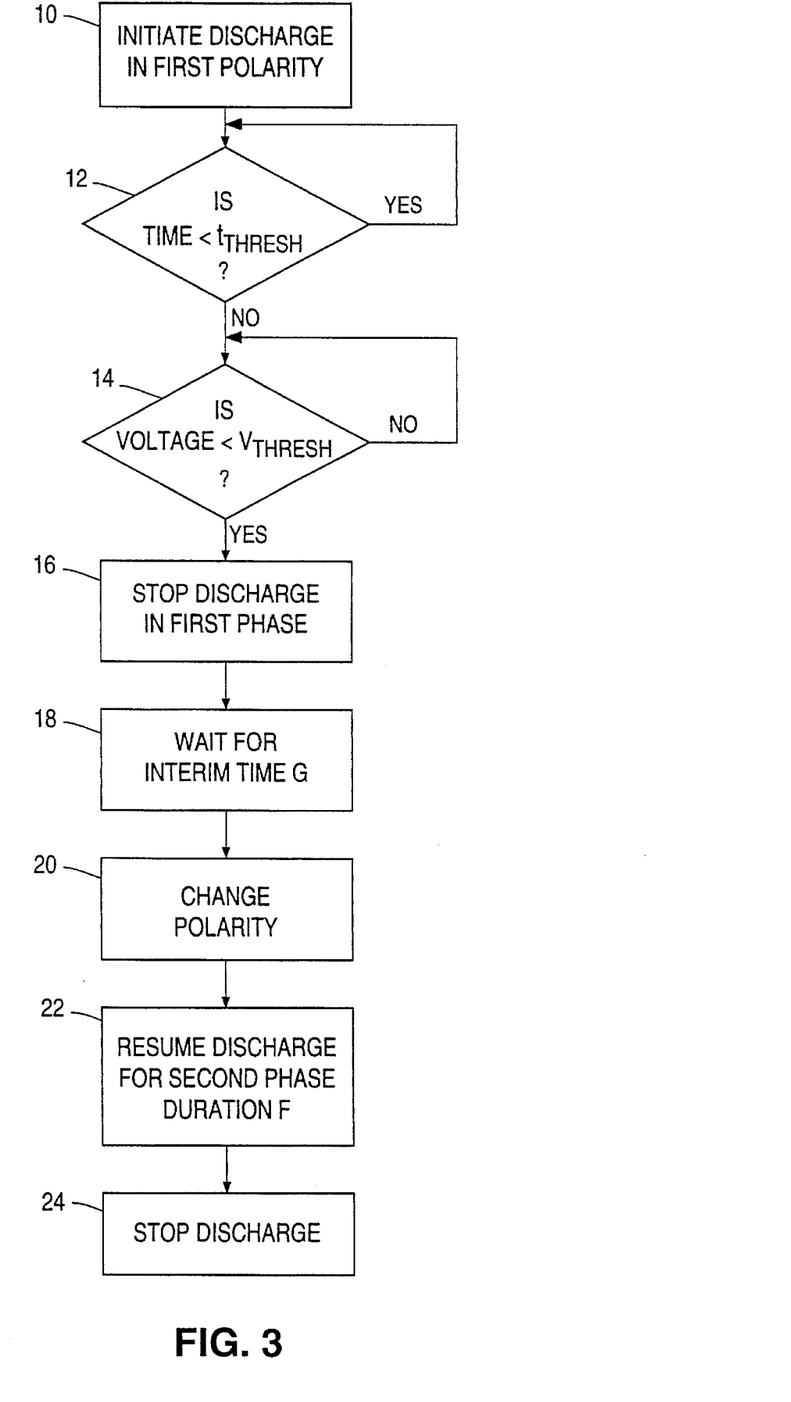
FIG. 3 is a flow chart demonstrating part of an electrotherapy method according to a second aspect of this invention.
Figure 4:
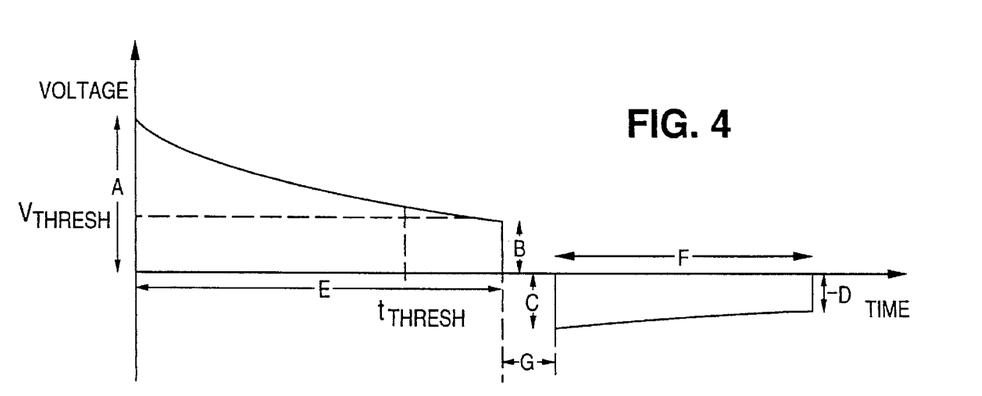
FIG. 4 is a schematic representation of a biphasic waveform delivered according to the second aspect of this invention.
Figure 5:
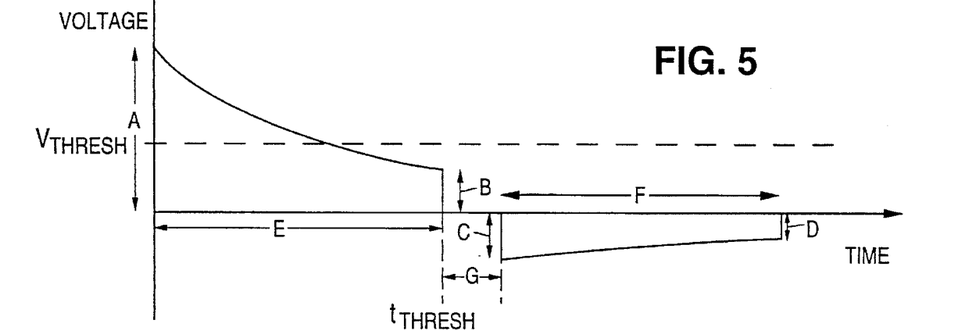
FIG. 5 is a schematic representation of a biphasic waveform delivered according to the second aspect of this invention.

Another feature of biphasic waveforms is that waveforms with relatively longer first phases have better conversion properties than waveforms with equal or shorter first phases, provided the total duration exceeds a critical minimum. Therefore, in the case of high impedance patients, it may be desirable to extend the first phase of the biphasic waveform (while the second phase duration is kept constant) to increase the overall efficacy of the electrotherapy by delivering a more efficacious waveform and to increase the total amount of energy delivered. FIGS. 3–5 demonstrate a defibrillation method according to this second aspect of the invention in which information related to patient impedance is fed back to the defibrillator to change the parameters of the delivered electrotherapeutic pulse.

FIG. 3 is a flow chart showing the method steps following the decision (by an operator or by the defibrillator itself) to apply an electrotherapeutic shock to the patient through electrodes attached to the patient and charging of the energy source, e.g., the defibrillator's capacitor or capacitor bank, to the initial first phase voltage A. Block 10 represents initiation of the first phase of the pulse in a first polarity. Discharge may be initiated manually by the user or automatically in response to patient heart activity measurements (e.g., ECG signals) received by the defibrillator through the electrodes and analyzed by the defibrillator controller in a manner known in the art.

Discharge of the first phase continues for at least a threshold time $t_{THRESH}$, as shown by block 12 of FIG. 3. If, at the end of time $t_{THRESH}$, the voltage measured across the energy source has not dropped below the minimum first phase terminal voltage threshold $V_{THRESH}$, first phase discharge continues, as shown in block 14 of FIG. 3. For high impedance patients, this situation results in an extension of the first phase duration beyond $t_{THRESH}$, as shown in FIG. 4, until the measured voltage drops below the threshold $V_{THRESH}$. Discharge then ends to complete the first phase, as represented by block 16 of FIG. 3. If, on the other hand, the patient has low impedance, the voltage will have dropped below $V_{THRESH}$ when the time threshold is reached, resulting in a waveform like the one shown in FIG. 5.

At the end of the first phase, and after a predetermined interim period G, the polarity of the energy source connection to the electrodes is switched, as represented by blocks 18 and 20 of FIG. 3. Discharge of the second phase of the biphasic pulse then commences and continues for a predetermined second phase duration F, as represented by block 22 of FIG. 3, then ceases. This compensating electrotherapy method ensures that the energy is delivered by the defibrillator in the most efficacious manner by providing for a minimum waveform tilt and by extending the first phase duration to meet the requirements of a particular patient.

Because this method increases the waveform tilt for high impedance patients and delivers more of the energy from the energy source than a method without compensation, the defibrillator's energy source can be smaller than in prior art external defibrillators, thereby minimizing defibrillator size, weight and expense. It should be noted that the waveforms shown in FIGS. 4 and 5 could be expressed in terms of current versus time using a predetermined current threshold value without departing from the scope of the invention.

Figure 6:
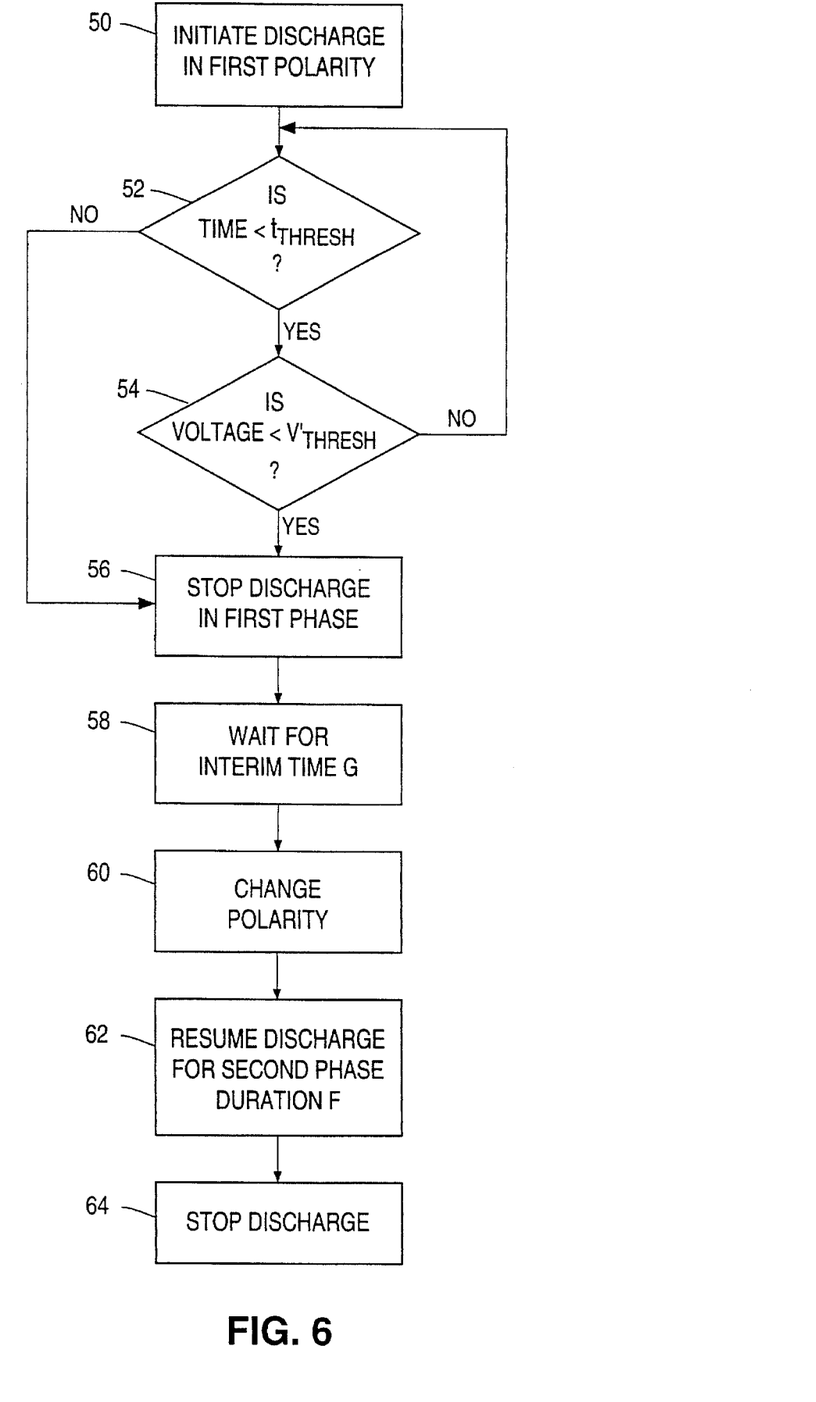
FIG. 6 Is a flow chart demonstrating part of an electrotherapy method according to a third aspect of this invention.
Figure 7:
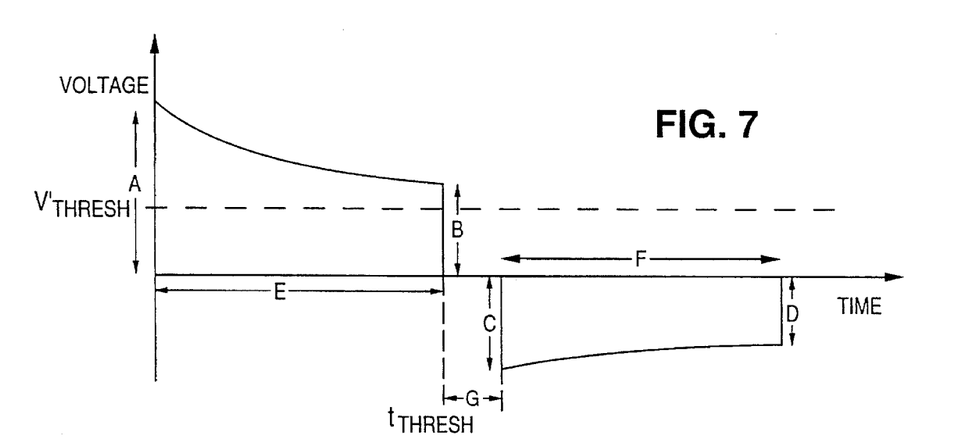
FIG. 7 is a schematic representation of a biphasic waveform delivered according to the third aspect of this invention.
Figure 8:
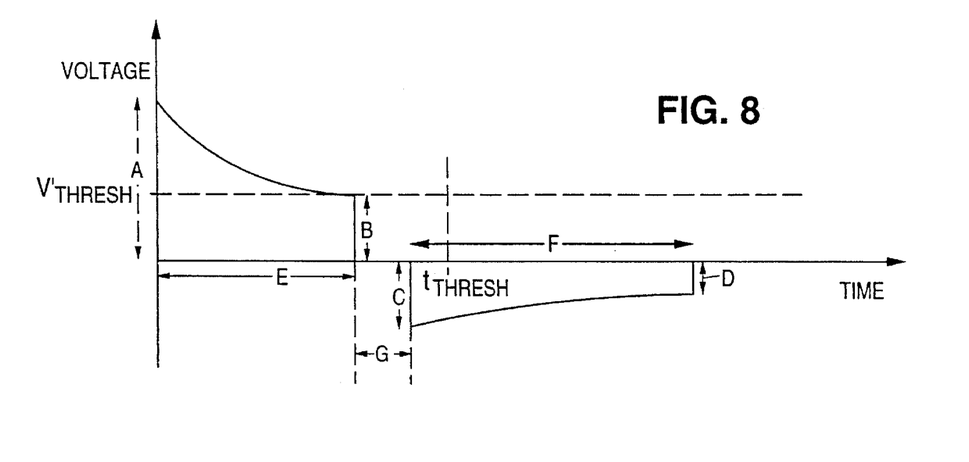
FIG. 8 is a schematic representation of a biphasic waveform delivered according to the third aspect of this invention.

FIGS. 6–8 illustrate a third aspect of this invention that prevents the delivered waveform from exceeding a maximum tilt (i.e., maximum delivered energy) in low impedance patients. As shown by blocks 52 and 54 in FIG. 6, the first phase discharge stops either at the end of a predetermined time $t_{THRESH}$ or when the first phase voltage drops below $V'_{THRESH}$. The second phase begins after an interim period G and continues for a preset period F as in the second aspect of the invention. Thus, in high impedance patients, the first phase ends at time $t_{THRESH}$, even if the voltage has not yet fallen below $V'_{THRESH}$, as shown in FIG. 7. In low impedance patients, on the other hand, the first phase of the delivered waveform could be shorter in duration than the time $t_{THRESH}$, as shown in FIG. 8.

Once again, the waveforms shown in FIGS. 7 and 8 could be expressed in terms of current versus time using a predetermined current threshold value without departing from the scope of the invention.

Figure 9:
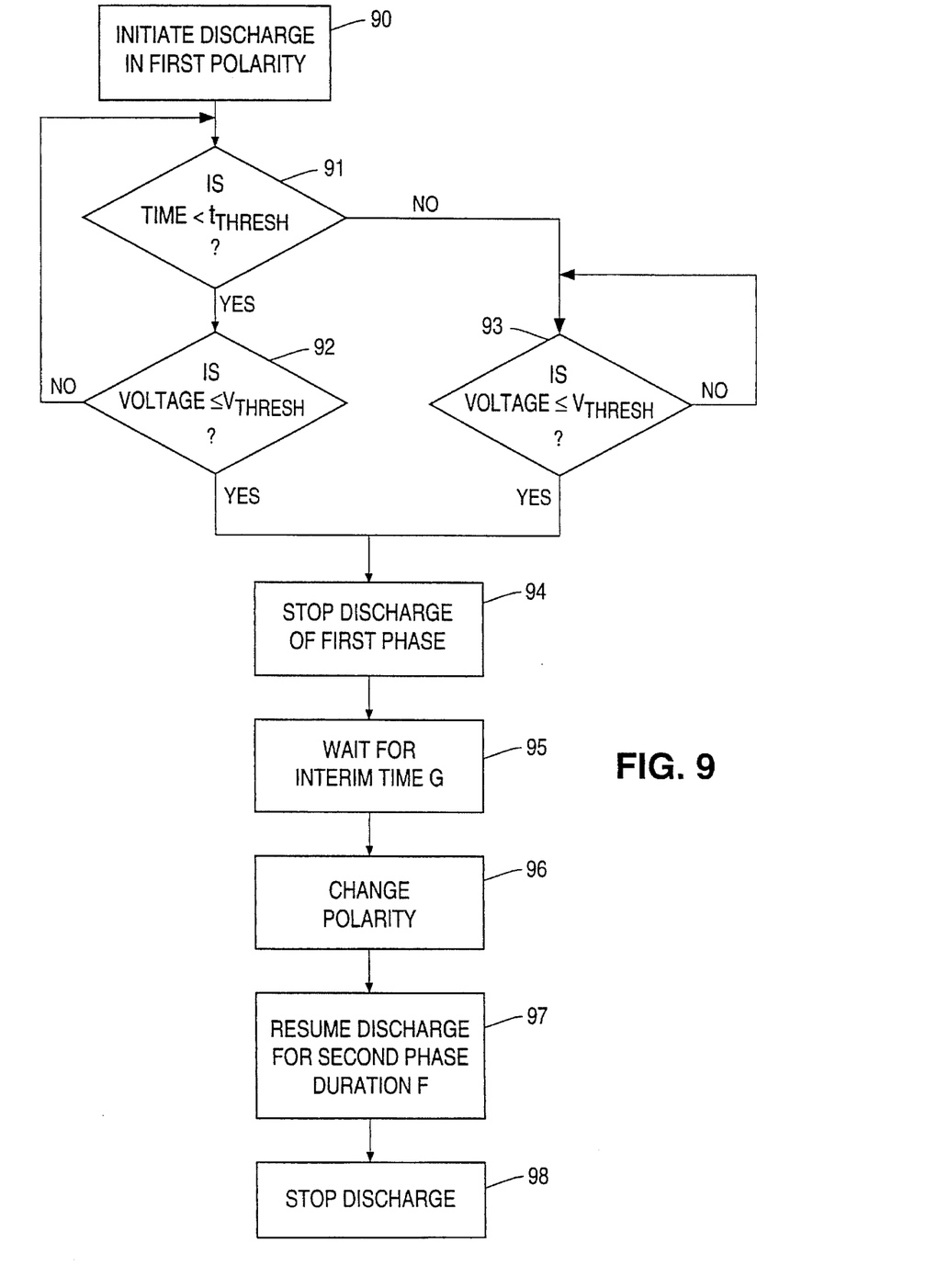
FIG. 9 is a flow chart demonstrating part of an electrotherapy method according to a combination of the second and third aspects of this invention.

FIG. 9 is a flow chart illustrating a combination of the defibrillation methods illustrated in FIGS. 3 and 6. In this combination method, the first phase of the biphasic waveform will end if the voltage reaches a first voltage threshold $V'_{THRESH}$ prior to the first phase duration threshold $t_{THRESH}$, as shown by blocks 91 and 92. This defibrillator decision path delivers a waveform like that shown in FIG. 8 for low impedance patients. For high impedance patients, on the other hand, if at the expiration of $t_{THRESH}$ the voltage has not fallen below $V'_{THRESH}$, the duration of the first phase is extended beyond $t_{THRESH}$ until the voltage measured across the electrodes reaches a second voltage threshold $V_{THRESH}$, as shown in decision blocks 91 and 93. This defibrillator method path will deliver a waveform like that shown in FIG. 4.

In alternative embodiments of this invention, the second phase pulse could be a function of the first phase voltage, current or time instead of having a fixed time duration. In addition, any of the above embodiments could provide for alternating initial polarities in successive monophasic or biphasic pulses. In other words, if in the first biphasic waveform delivered by the system the first phase is a positive voltage or current pulse followed by a second phase negative voltage or current pulse, the second biphasic waveform delivered by the system would be a negative first phase voltage or current pulse followed by a positive second phase voltage or current pulse. This arrangement would minimize electrode polarization, i.e., build-up of charge on the electrodes.

For each defibrillator method discussed above, the initial first phase voltage A may be the same for all patients or it may be selected automatically or by the defibrillator user. For example, the defibrillator may have a selection of initial voltage settings, one for an infant, a second for an adult, and a third for use in open heart surgery.

Figure 10:
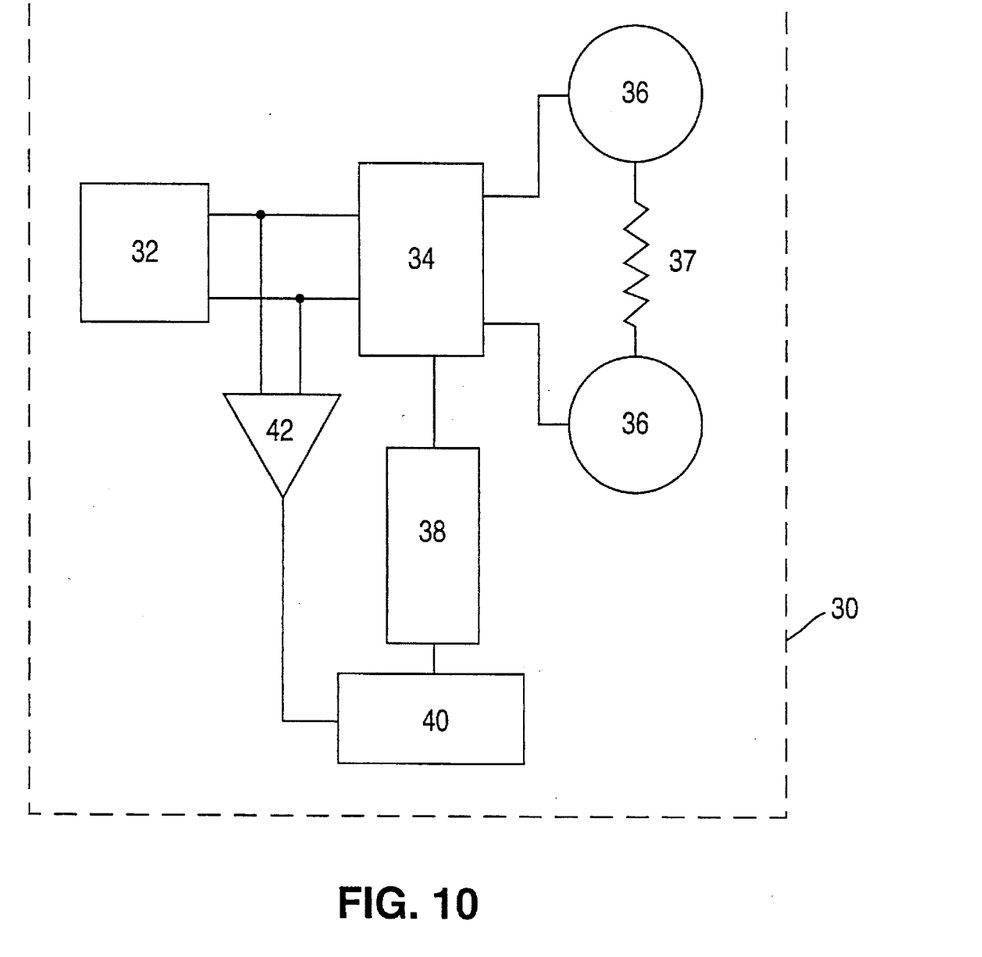
FIG. 10 is a block diagram of a defibrillator system according to a preferred embodiment of this invention.

FIG. 10 is a schematic block diagram of a defibrillator system according to a preferred embodiment of this invention. The defibrillator system 30 comprises an energy source 32 to provide the voltage or current pulses described above. In one preferred embodiment, energy source 32 is a single capacitor or a capacitor bank arranged to act as a single capacitor. A connecting mechanism 34 selectively connects and disconnects energy source 32 to and from a pair of electrodes 36 electrically attached to a patient, represented here as a resistive load 37. The connections between the electrodes and the energy source may be in either of two polarities with respect to positive and negative terminals on the energy source.

The defibrillator system is controlled by a controller 38. Specifically, controller 38 operates the connecting mechanism 34 to connect energy source 32 with electrodes 36 in one of the two polarities or to disconnect energy source 32 from electrodes 36. Controller 38 receives timing information from a timer 40, and timer 40 receives electrical information from electrical sensor 42 connected across energy source 32. In some preferred embodiments, sensor 42 is a voltage sensor; in other preferred embodiments, sensor 42 is a current sensor.

Figure 11:
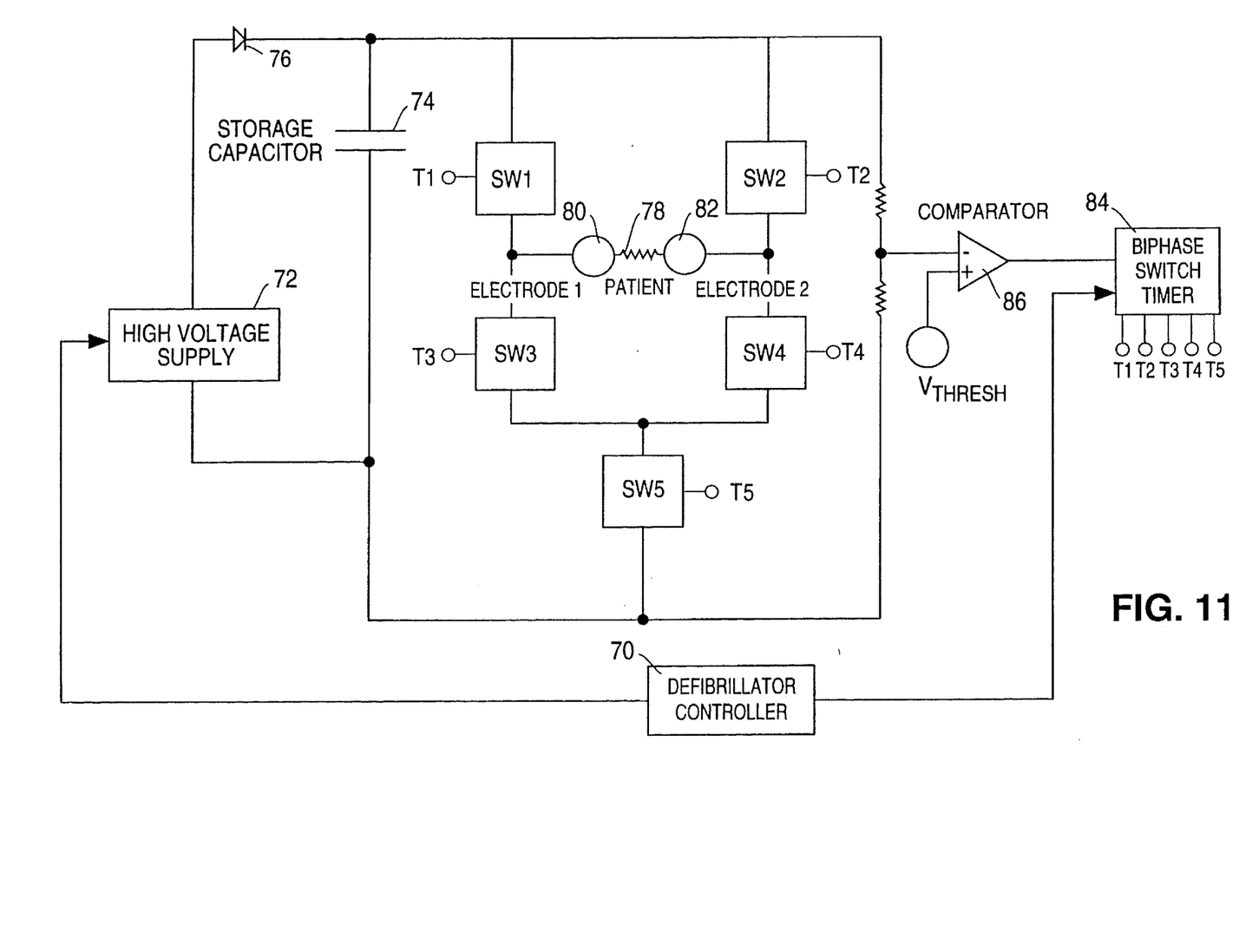
FIG. 11 is a schematic circuit diagram of a defibrillator system according to a preferred embodiment of this invention.

FIG. 11 is a schematic circuit diagram illustrating a device according to the preferred embodiments discussed above. Defibrillator controller 70 activates a high voltage power supply 72 to charge storage capacitor 74 via diode 76 to a predetermined voltage. During this period, switches SW1, SW2, SW3 and SW4 are turned off so that no voltage is applied to the patient (represented here as resistor 78)

connected between electrodes 80 and 82. SW5 is turned on during this time.

After charging the capacitor, controller 70 de-activates supply 72 and activates biphase switch timer 84. Timer 84 initiates discharge of the first phase of the biphasic waveform through the patient in a first polarity by simultaneously turning on switches SW1 and SW4 via control signals T1 and T4, while switch SW5 remains on to deliver the initial voltage A through electrodes 80 and 82 to the patient 78.

Depending on the operating mode, delivery of the first phase of the biphasic pulse may be terminated by the timer 84 after the end of a predetermined period or when the voltage across the electrodes has dropped below a predetermined value as measured by comparator 86. Timer 84 terminates pulse delivery by turning off switch SW5 via control signal T5, followed by turning off switches SW1 and SW4. The voltage across electrodes 80 and 82 then returns to zero.

During the interim period G, SW5 is turned on to prepare for the second phase. After the end of interim period G, timer 84 initiates delivery of the second phase by simultaneously turning on switches SW2 and SW3 via control signals T2 and T3 while switch SW5 remains on. This configuration applies voltage from the capacitor to the electrodes at an initial second phase voltage C and in a polarity opposite to the first polarity. Timer 84 terminates delivery of the second phase by turning off switch SW5 via control signal T5, followed by turning off switches SW2 and SW3. The second phase may be terminated at the end of a predetermined period or when the voltage measured by comparator 86 drops below a second phase termination voltage threshold.

In a preferred embodiment, switch SW5 is an insulated gate bipolar transistor (IGBT) and switches SW1–SW4 are silicon-controlled rectifiers (SCRs). The SCRs are avalanche-type switches which can be turned on to a conductive state by the application of a control signal, but cannot be turned off until the current through the switch falls to zero or near zero. Thus, the five switches can be configured so that any of the switches SW1–SW4 will close when SW5 is closed and will reopen only upon application of a specific control signal to SW5.

This design has the further advantage that switch SW5 does not need to withstand the maximum capacitor voltage. The maximum voltage that will be applied across switch SW5 will occur when the first phase is terminated by turning SW5 off, at which time the capacitor voltage has decayed to some fraction of its initial value.

Other switches and switch configurations may be used, of course without departing from the scope of the invention. In addition, the defibrillator configurations of FIGS. 10 and 11 may be used to deliver electric pulses of any polarity, amplitude, and duration singly and in any combination.

While the invention has been discussed with reference to external defibrillators, one or more aspects of the invention would be applicable to implantable defibrillators as well. Other modifications will be apparent to those skilled in the art.

What is claimed is:

1. A method for applying electrotherapy to a patient through electrodes connected to an energy source, the method comprising the following steps:

discharging the energy source across the electrodes to deliver electrical energy to the patient in a multiphasic waveform;

monitoring a patient-dependent electrical parameter during the discharging step;

adjusting a discharge parameter of a later phase of the multiphasic waveform as a function of a value of the electrical parameter during an earlier phase.

2. The method of claim 1 further comprising discharging the energy source across the electrodes in the earlier phase until the end of a predetermined time period and until the electrical parameter reaches a predetermined value.

3. The method of claim 1 wherein the electrical parameter is energy source voltage.

4. The method of claim 1 wherein the electrical parameter is energy source current.

5. The method of claim 1 wherein the waveform comprises a truncated exponential biphasic waveform.

* * * * *

UNITED STATES PATENT AND TRADEMARK OFFICE
CERTIFICATE OF CORRECTION

PATENT NO. : 5,601,612
DATED : February 11, 1997
INVENTOR(S) : Bradford E. Gliner, et al It is certified that error appears in the above-indentified patent and that said Letters Patent is hereby corrected as shown below:

In column 3, at line 46, the equation: "$H=|A|-|D|/|A|X100$" should be:

$$H = \frac{|A| - |D|}{|A|} \times 100$$

Signed and Sealed this

Eleventh Day of November, 1997

*Attest:*

BRUCE LEHMAN

*Attesting Officer*     *Commissioner of Patents and Trademarks*